United States Patent [19]

Kurowski et al.

[11] Patent Number: 5,544,657
[45] Date of Patent: Aug. 13, 1996

[54] ULTRASOUND BLOOD FLOW MONITOR OF THE NON-DOPPLER TYPE

[75] Inventors: Lorenz V. Kurowski, Princeton; Wolf-Ekkehard Blanz, Belle Mead, both of N.J.; Wolf Delong, Mercer Island, Wash.

[73] Assignee: Siemens Medical Systems, Inc., Iselin, N.J.

[21] Appl. No.: 304,103
[22] Filed: Sep. 9, 1994
[51] Int. Cl.⁶ .................................................. A61B 8/00
[52] U.S. Cl. .................................................. 128/661.08
[58] Field of Search ................... 128/660.05, 661.01, 128/661.08, 661.09, 661.10, 916, 660.07, 661.03, 661.02; 73/861.25, 861.26

[56] References Cited

U.S. PATENT DOCUMENTS

| | | | |
|---|---|---|---|
| 4,587,973 | 5/1986 | Flax | 128/661.03 |
| 4,790,321 | 12/1988 | Miwa et al. | 128/660.07 |
| 4,928,698 | 5/1990 | Bonnefous | 128/661.09 |
| 5,022,400 | 6/1991 | Walters | 128/661.09 |
| 5,081,993 | 1/1992 | Kitney et al. | 128/661.08 |
| 5,105,816 | 4/1992 | Shimura et al. | 128/661.08 |
| 5,360,007 | 11/1994 | Shinomura et al. | 128/661.01 |

*Primary Examiner*—George Manuel

[57] ABSTRACT

Reflected-back ultrasound waves are recorded and rebinned in accordance with a particular data classification scheme. In a post processing step, the data is processed to remove the effect of stationary scatterers (such as slowly-moving body structure) and features of the processed data are computer-traced to determine e.g. the velocity of the patient's blood stream.

3 Claims, 6 Drawing Sheets

ULTRASOUND BLOOD FLOW MONITOR OF THE NON-DOPPLER TYPE

BACKGROUND OF THE INVENTION

The invention relates to medical diagnostic equipment, and more particularly relates to equipment which uses ultrasound to diagnose a patient's medical condition. In its most immediate sense, the invention relates to ultrasound blood flow monitors.

In conventional ultrasound blood flow monitors, the velocity of the patient's blood flow is determined using the Doppler effect. In such apparatus, an insonifying sound wave is reflected back by the patient's blood. According to the Doppler effect, the frequency shift in the reflected-back wave relative to the insonifying wave (the "Doppler shift") is determined by the velocity of the patient's blood flow, and conventional blood flow apparatus measures this frequency shift so the diagnostician can know the direction and speed with which the patient's blood is flowing.

Because the Doppler shift is quite small as compared with the frequency of the insonifying sound wave, it cannot be determined accurately on the basis of only one reflected-back sound wave. A plurality of such reflected-back sound waves must be considered, and it is necessary to compute the autocorrelation of the Doppler shift using all the reflected-back signals to arrive at an accurate estimate of the patient's blood flow velocity. Such computation requires substantial computer resources.

It would be advantageous to provide alternate ultrasound method and apparatus for measuring the velocity of a moving scatterer (e.g. the patient's blood stream) which would not require intensive computation (thereby reducing the need for high-performance computer resources).

The invention proceeds from the realization that as a series of insonifying sound waves are reflected back from a moving scatterer, such as the patient's blood stream, successively reflected-back sound waves are time-shifted as a function of the velocity of the scatterer. Thus, in accordance with the invention, the displacement of corresponding wavefronts in the reflected-back sound waves is determined and used to compute the velocity of the scatterer. In accordance with the preferred embodiment of the invention, a feature in each of the reflected-back sound waves is identified and the movement of that feature is traced. By using a feature-tracing scheme, computation of scatterer velocity is greatly simplified.

Advantageously, apparatus in accordance with the preferred embodiment of the invention records in real time the "raw" ultrasound information accumulated by the transducer while in receive mode. This information is stored and scatterer velocity is determined periodically in real time each time sufficient data has been acquired. To do this, the data is processed by simple subtraction to remove information which relates to stationary scatterers. The remaining information relates to moving scatterers, such as the patient's blood. Advantageously, a computer search strategy can be used to extract velocity-related information; little if any computation is required.

BRIEF DESCRIPTION OF THE DRAWINGS

The invention will be better understood with reference to the following illustrative and non-limiting drawings, in which.

DETAILED DESCRIPTION OF PREFERRED EMBODIMENTS

Figure 1:
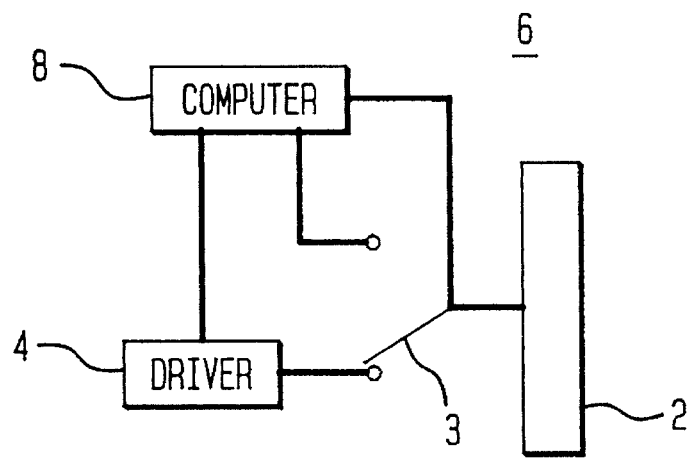
FIG. 1 is a block diagram of apparatus in accordance with the preferred embodiment of the invention.

An ultrasound imaging system in accordance with the preferred embodiment of the invention utilizes a transducer 2. When the transducer 2 is operated in the transmit mode by suitable operation of a switching circuit schematically shown as switch 3, the transducer 2 is connected to a driver circuit 4 which supplies electrical signals to the transducer 2 under control of a computer 8. This causes the transducer 2 to send out ultrasonic signals (not shown) toward a patient 6. These insonifying signals are reflected back from the patient 6. When the reflected-back signals (not shown) are incident upon the transducer 2 and the transducer 2 is operated in the receive mode by appropriate operation of the switch 3, the reflected-back signals are converted into electrical signals which are routed to the computer 8. The computer 8 then, and using the methodology described below, determines the direction and velocity of the patient's blood stream within the insonified region of the patient 6. In practice, the switch 3 is operated to place the transducer 2 in receive mode at regular intervals. This has the effect of sampling reflected-back signals from different depths within the patient 6 since the speed of propagation of the ultrasound signals is constant within the patient 6.

In the following description, it should be understood that an ultrasound image contains information from stationary scatterers and also from moving scatterers. Since most of the patient's body structure remains relatively stationary during an ultrasound study, information from stationary scatterers greatly predominates. Thus, a blood flow monitor must extract a relatively small quantity of comparatively low-amplitude information from a relatively large quantity of comparatively high-amplitude information.

The description below will initially describe the basic physics of ultrasound imaging in accordance with the invention. Thereafter, methodology in accordance with the preferred embodiment of the invention will be described in some detail.

Figure 2:
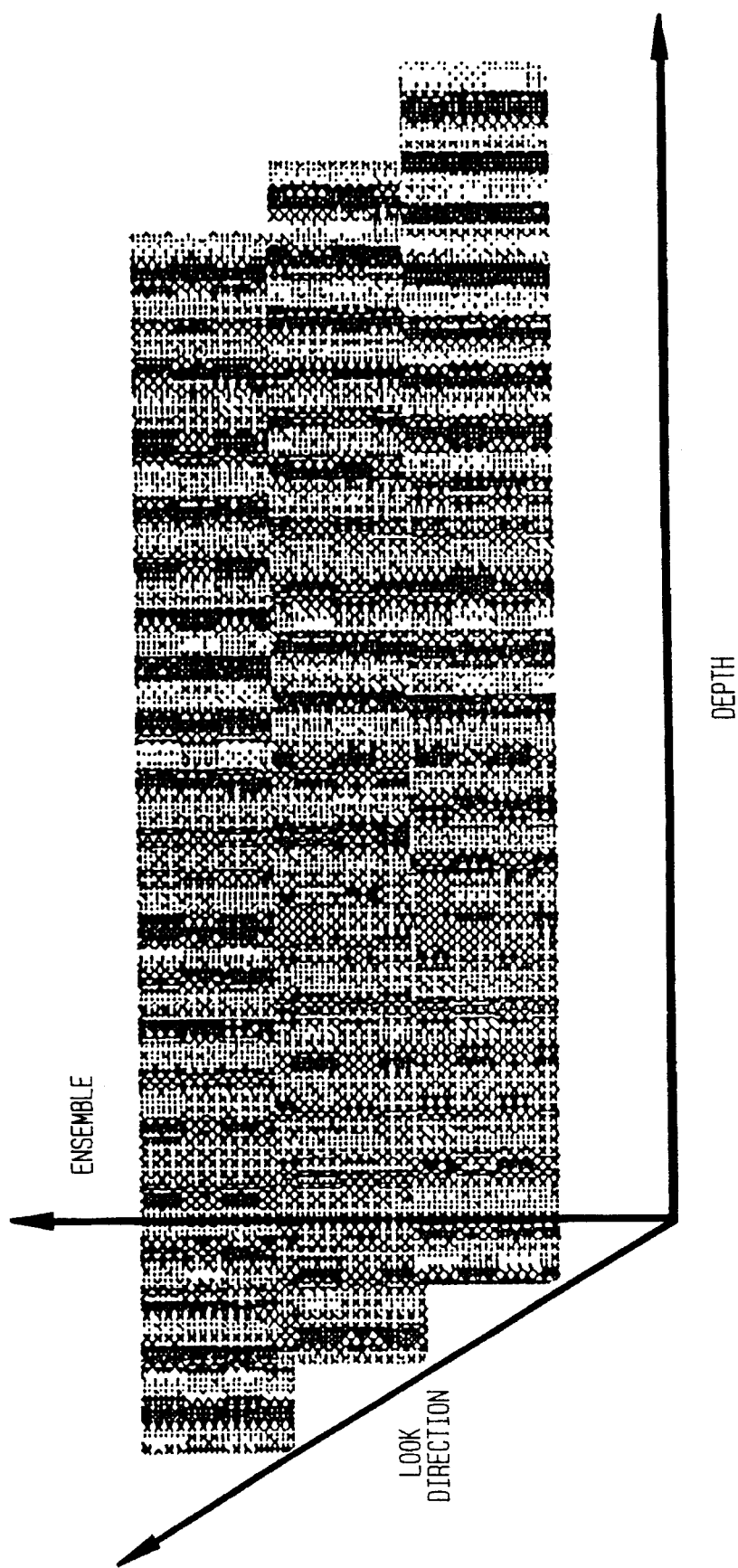
FIG. 2 schematically depicts the constructive and destructive interference which results from the reflection back of an insonifying pulse from a group of absolutely stationary scatterers.

Let it be assumed that an insonifying signal is directed along a particular "look direction" and is reflected back by many scatterers at the same depth within a patient (As used herein, "depth" refers to distance between the scatterers and the ultrasound transducer, which is placed upon the skin of the patient 6. This is known to persons skilled in the art.) An insonifying signal is periodic (usually sinusoidal). The result of such reflection back is a superposition of the many signals which are reflected back from the scatterers. These signals constructively and destructively interfere with each other. In FIG. 2, such constructive and destructive interference is shown using an image format. Each row in FIG. 2 corresponds to an "ensemble" of signals which are reflected back along the same look direction by all scatterers at a particular depth within the patient 6. Along each such row, the constructive and destructive interference between the reflected-back signals produces the characteristic pattern of points, with the darkest points and lightest points representing regions of maximum positive amplitude (maximum constructive interference) and medium-grey points representing regions of approximately zero amplitude (maximum destructive interference). Together, the rows form the characteristic fringe pattern.

Where all scatterers are stationary (this is the case for FIG. 2 as shown) and the ensembles of reflected-back signals are juxtaposed as shown, the above-described points will form lines which are absolutely parallel to the ensemble direction. In other words, for stationary scatterers at the same depth which reflect back waves coming from the same look direction, the interference patterns formed by the reflected-back waves are likewise stationary; they do not move from one ensemble to the next. However, this is not so where the scatterers are moving, and this instance will now be discussed with reference to FIGS. 3, 4 and 5.

Let it be assumed that a group of scatterers ceases to be stationary and begins to move together with absolute synchrony. At any given instant of time, this group will reflect back a wave which has the appearance of one of the above-described rows in FIG. 2. However, since the group of scatterers is moving, the reflected-back wave will move with it.

Figure 3:
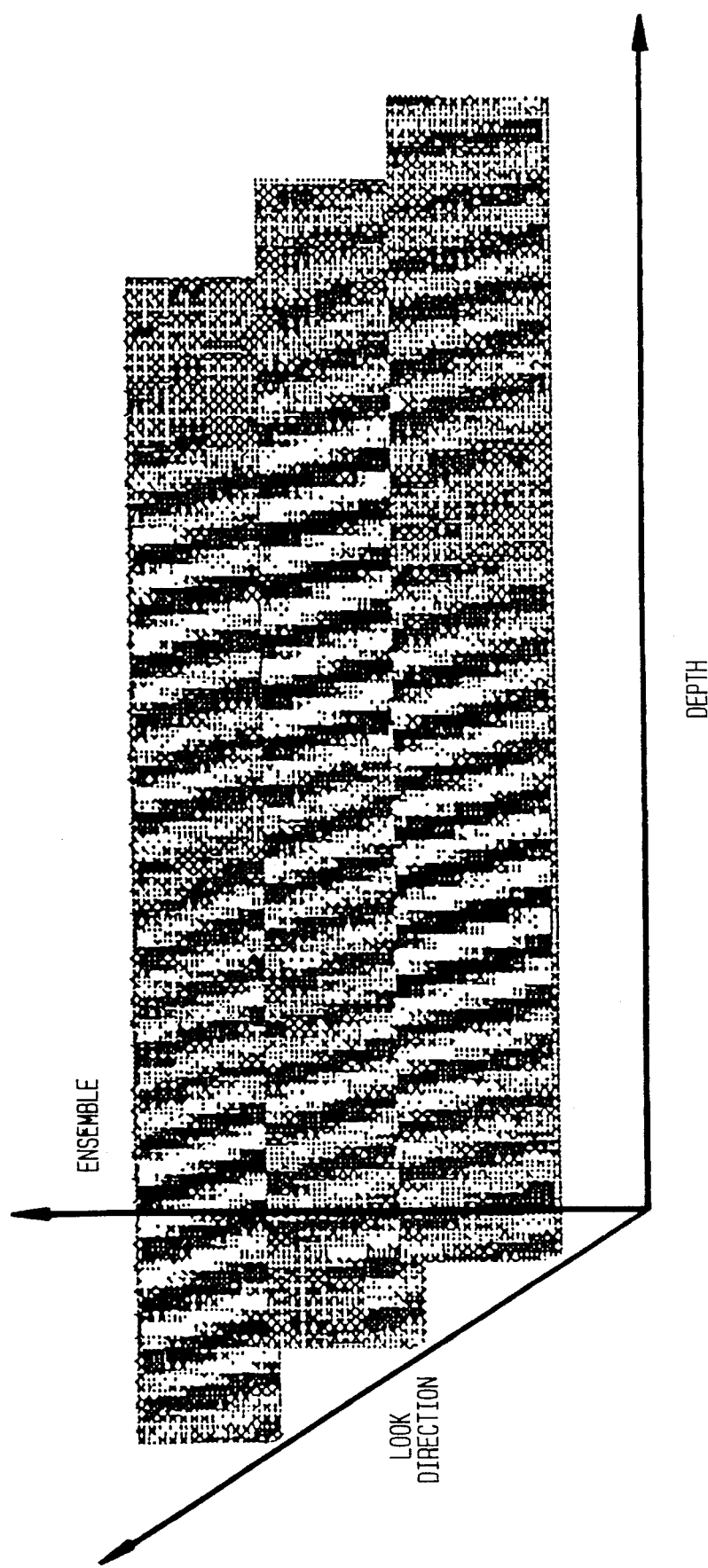
FIG. 3 schematically depicts the constructive and destructive interferences which result from the reflection back of an insonifying pulse from a group of moving scatterers.

Let it be further assumed that this group of scatterers moves, and that a component of this motion is exactly parallel to the depth direction (i.e. exactly normal to the transducer 2, and to the left as viewed in FIG. 2). In this case, the row relating to the second ensemble will be displaced leftwardly as compared to the row relating to the first ensemble. Furthermore, the row relating to the third ensemble will be displaced leftwardly as compared to the row relating to the second ensemble. The result will be a pattern such as is illustrated in FIG. 3.

Figure 5:
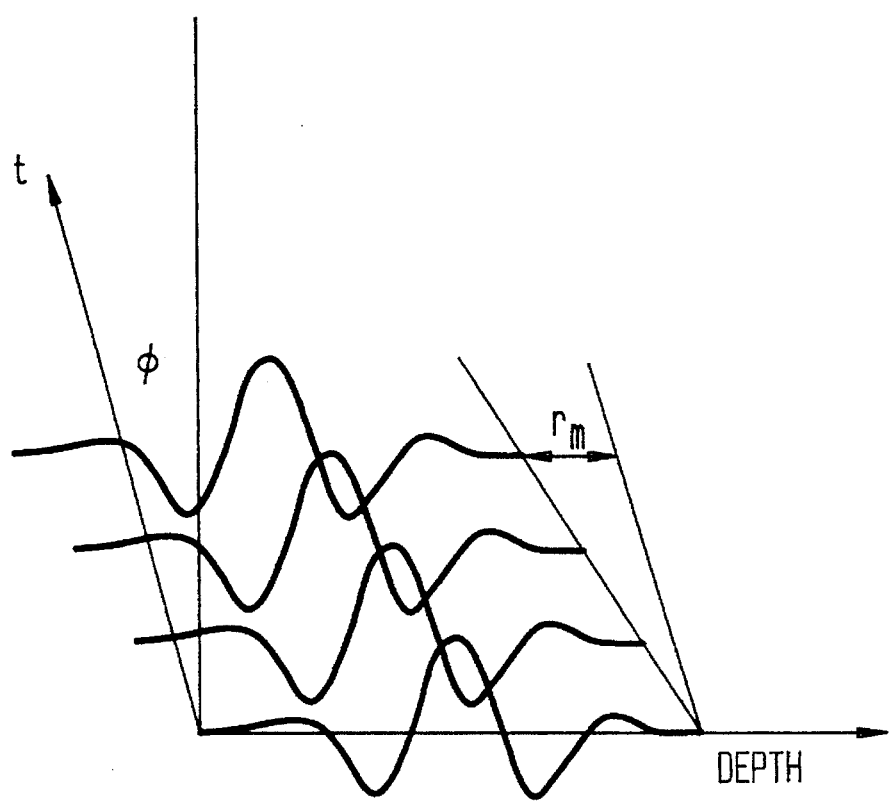
FIG. 5 schematically shows the wave front of the ultrasound wave in accordance with FIG. 4.
Figure 4:
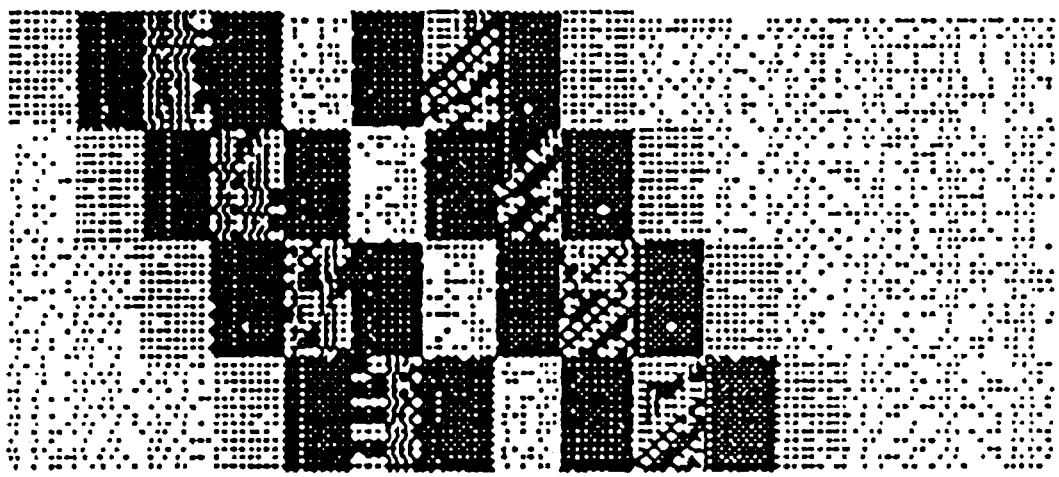
FIG. 4 schematically depicts the appearance of a part of a band as shown in FIG. 3.

Turning now to FIGS. 4 and 5 (which show, respectively, an enlarged region of FIG. 3 and the actual waveform of the reflected-back ultrasound wave), it is apparent that the above-described lines will no longer be parallel to the ensemble direction. These lines will rather be inclined at a slope $\phi$ to the ensemble direction (FIG. 5), and the slope $\phi$ will vary with velocity of the scatterer group; negative $\phi$'s will indicate motion towards the transducer 2, positive $\phi$'s will indicate motion away from the transducer 2, and the magnitude of $\phi$ will reflect the speed of the scatterer group.

The above description has proceeded upon the assumption that a group of scatterers moves with absolute synchrony. This assumption is inaccurate as applied to the bloodstream of a human patient. A patient's bloodstream never moves in a perfect laminar flow; different parts of the bloodstream move at different speeds and along different directions. For this reason, in a blood flow monitor in accordance with the preferred embodiment of the invention, the above-described lines will never be absolutely straight; they will rather curve gently in one direction and another.

Furthermore, the "raw" data from the transducer 2 (when used in a blood flow monitor in accordance with the preferred embodiment) will seldom if ever exhibit the slope $\phi$ which is shown in FIG. 5. It will be recalled that moving scatterers, such as blood cells in the patient's bloodstream, account for only a small fraction of the information at the output of the transducer 2. Such information is not merely dominated, but is indeed overwhelmed, by stationary scatterers (which, it will be recalled, produce lines of constant intensity that are parallel to the ensemble direction). It is therefore necessary to remove information relating to stationary scatterers so as to make manifest information which relates to the moving scatterers.

In accordance with the preferred embodiment of the invention, this is done by storing, in real time, the "raw" ultrasound data at the output of the transducer 2. (In this, apparatus in accordance with the preferred embodiment differs from conventional ultrasound blood flow apparatus. Conventional ultrasound blood flow apparatus works on a "pipeline" principle; data coming in is processed serially in real time and is never stored in "raw" form.) The data is then rebinned so that it is organized in accordance with the format illustrated in FIGS. 2 and 3, i.e. so that rows are parallel to the depth axis and columns are parallel to the ensemble direction. Then, in a subsequent step, the computer 8 goes up (or down) the columns, successively computing and storing the difference between each two adjacent elements in the column under consideration.

Where the difference is zero, this means that the two elements are unaffected by moving scatterers. Where the difference is nonzero, the difference reflects scatterer motion. Thus, by subtracting neighboring pairs of elements in the same column of data, the dominant (and constant) influence of the stationary scatterers is removed. This leaves only the information resulting from moving scatterers, which information will produce lines having the above-described slope $\phi$.

In accordance with the preferred embodiment of the invention, the slope $\phi$ is determined by identifying features in the thus-processed "raw" ultrasound data from the transducer 2. Advantageously, and in accordance with the preferred embodiment, the system uses a search scheme which "looks" for zero crossovers and connects them together along lines. (Alternatively, the system could be programmed to "look" for local maxima or minima. This would require modification of the below-described search scheme. At present, use of zero-crossovers is considered to be the most expedient choice.) The system then correlates the beginning and end of one such line to determine the slope $\phi$. In this way, computational demands on the computer 8 are minimized.

Figure 6:
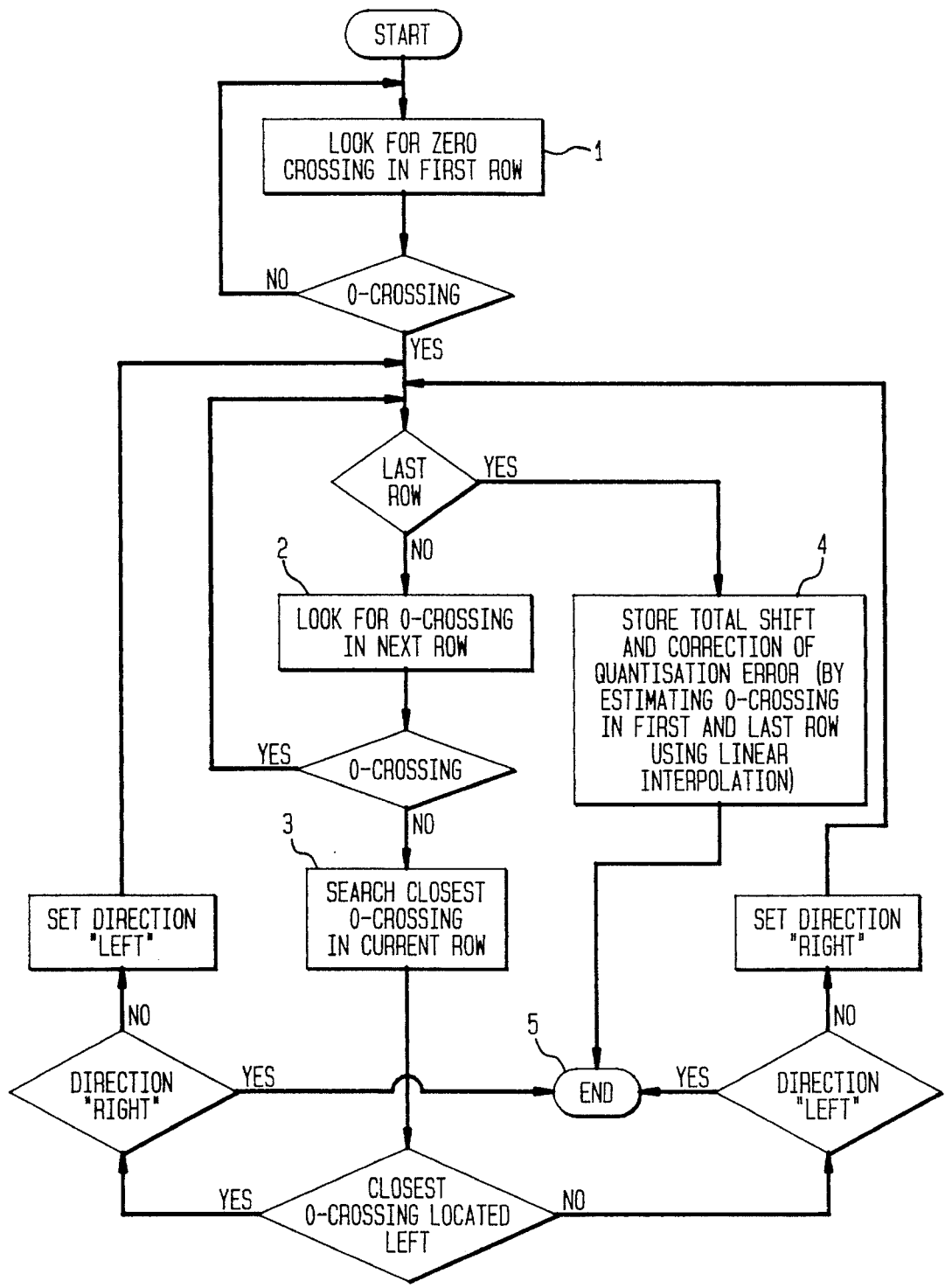
FIG. 6 is a flow chart which shows how a matrix of data from a band such as is shown in FIG. 3 can be computer-searched to identify scatterer velocity in accordance with the preferred embodiment of the invention.
Figure 7:
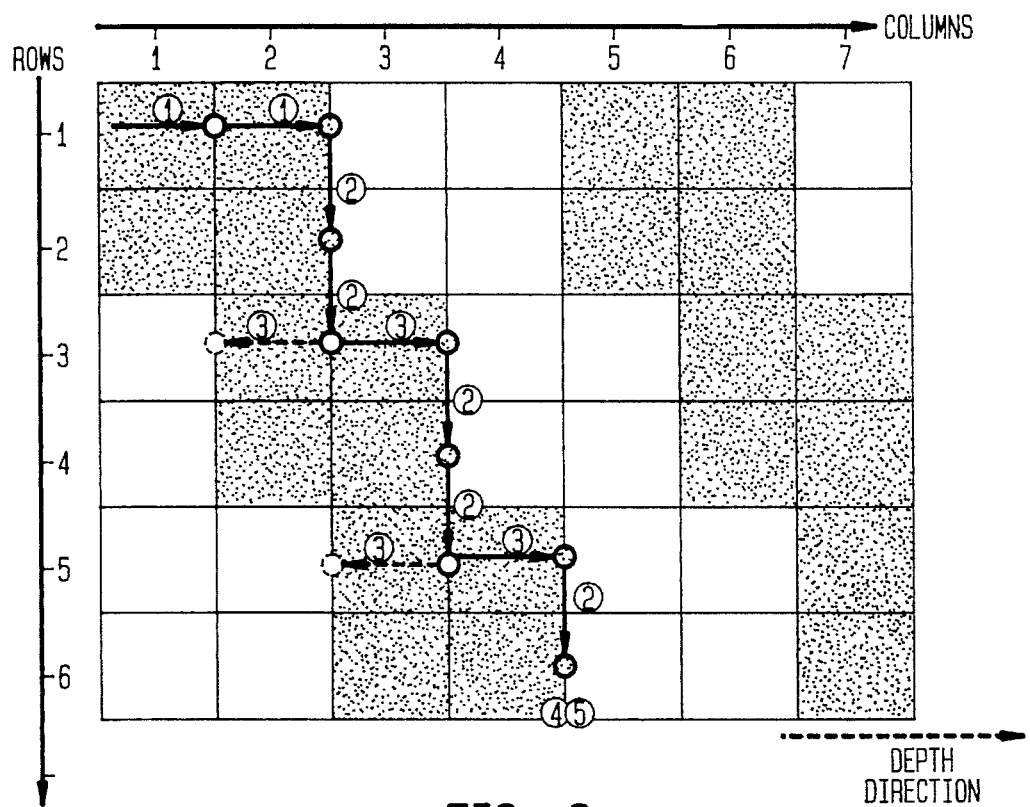
FIG. 7 is a matrix showing how the FIG. 6 computer search strategy works to find a feature pattern from which scatterer velocity can be determined.
Figure 8:
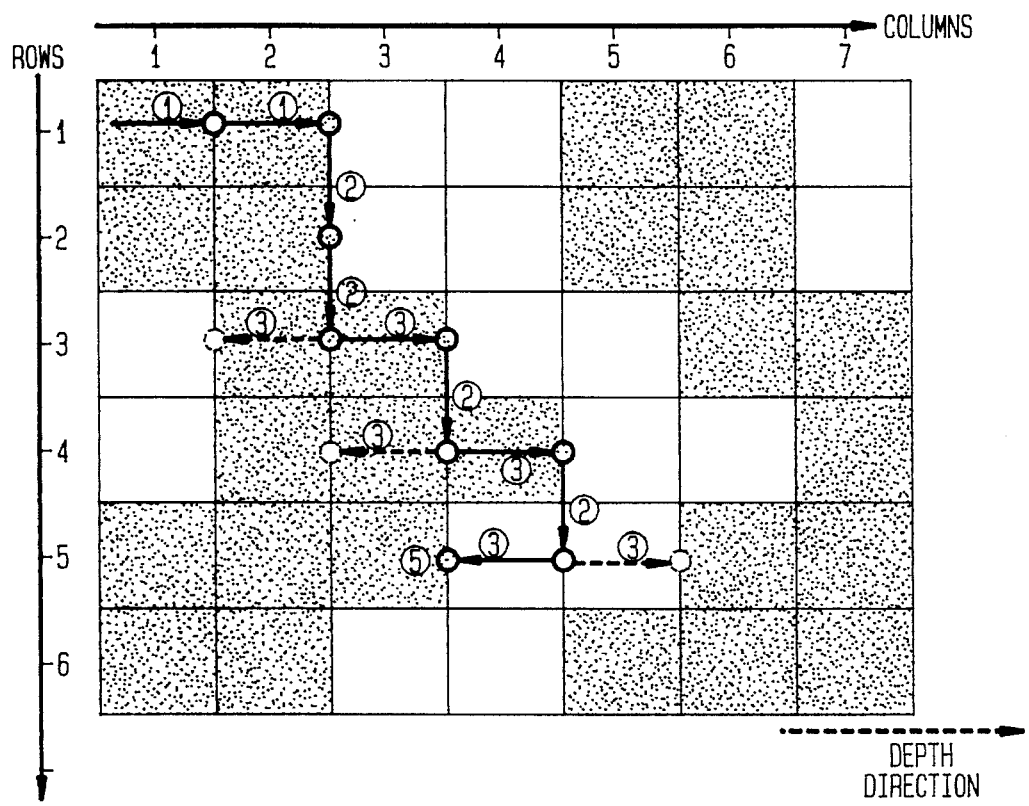
FIG. 8 is a matrix showing how the FIG. 6 computer search strategy works in the absence of a feature pattern from which scatterer velocity can be determined.

Reference will now be made to FIGS. 6, 7 and 8. In FIGS. 7 and 8, dark cells have values which are above zero and light cells have values which are below zero. Therefore, there is a zero crossover between adjacent cells of different color. Where a light cell is to the right of a dark cell along the depth direction, the zero crossover is "negative-going"; where a dark cell is to the right of a light cell along the depth direction, the zero crossover is "positive going".

The following description of the computer search strategy considers two cases. In the first, the data in the matrix is such that the slope $\phi$ can be determined. In the second, the data in the matrix is too noisy and the slope $\phi$ cannot be determined.

Referring to FIGS. 6 and 7 together, the search commences by setting to "NO DIRECTION" a direction variable which may be either "LEFT", "RIGHT" of "NO DIRECTION" and by comparing the value of the cell 1,1 to the value of the cell 1,2. There is no zero crossing, so the search continues by similarly comparing the contents of the cell 1,2 to those of the cell 1,3. Here, a negative-going zero crossover is detected, so in the description which follows, the system only "looks" for negative-going zero crossovers. If a positive-going zero crossover had been detected, the system would thereafter have looked exclusively for positive-going zero crossovers.

The current row is not the last row, so the search proceeds by proceeding to the next row. In the next row, the contents of the cell 2,2 are compared with the contents of the cell 2,3. Here again, there is a negative-going zero crossing, so the search continues by proceeding to the next row. When the contents of the cell 3,2 are compared with the contents of the cell 3,3, there is no zero crossing. At this point, the system continues searching for negative-going zero crossovers by moving left and right in the current row and identifying whether the closest negative-going zero crossover is located to the right of the boundry between cells 3,2 and 3,3 or to the left of that boundry. In the present instance, the closest negative-going zero crossover is located between cells 3,3 and 3,4. At this point, the system examines the state of the direction variable. Since the direction variable is "NO DIRECTION", the direction variable is not "LEFT". The direction variable is then set to "RIGHT" and the system checks to make sure that the current row is not the last row to be considered. Because row 3 is not the last row to be considered, the search strategy then continues to the next row, namely row 4.

The search strategy then proceeds to compare the contents of the cells in the next row, i.e. cells 4,3 and 4,4. Here again, there is a negative-going zero crossover, so the search proceeds to the next row and the contents of cells 5,3 and 5,4 are compared. There is no negative-going zero crossover, so the search proceeds to the left and to the right in row 5, looking for the closest negative-going zero crossover. As in the prior case, the closest such crossover is to the right, the direction variable is now set to "RIGHT" (i.e. not "LEFT") and the search proceeds to the last row, namely row 6.

Since row 6 is the last row, this search strategy has established that there is a unidirectional slope $\phi$, which can be simply calculated by determining the number of columns between the initially detected zero crossover and the finally detected zero crossover and whether the initially-detected zero crossover is to the left or to the right of the finally detected zero crossover.

In the case illustrated in FIG. 8, the search proceeds in the same way that it proceeded in FIG. 7, until the search compares the contents of the cells 4,3 and 4,4. This time, there is no zero crossing, so the system proceeds to look left and right to find out the location of the nearest negative-going zero crossover. This is located to the right, the direction variable is set to "RIGHT", and row 5 is not the last row. The search then proceeds down one row, and the contents of the cells 5,4 and 5,5 are compared.

There is no zero crossing between the cells 5,4 and 5,5. Thus, the system looks left and right to identify the location of the closest negative-going zero crossover. This is located between cells 5,3 and 5,4, which is to the left of the boundry between the cells 5,4 and 5,5. As a result, the search strategy comes to an end (it will be recalled that the direction variable is set to "RIGHT"). In qualitative terms, there is no unidirectional slope shown in FIG. 8, so no slope $\phi$ can be calculated.

In the above examples, the number of rows equalled six. This is not part of the invention; more or fewer rows can be used. Additionally, there need be no one-to-one correspondence between the number of ensembles acquired during a particular portion of an ultrasound blood flow study and the number of rows; it would e.g. be possible to use only every other ensemble as a basis for searching or to limit searching to predetermined regions within such ensembles.

Although a preferred embodiment has been described above, the scope of the invention is limited only by the following claims:

We claim:

1. A method of measuring the velocity of a moving scatterer using ultrasound, comprising the steps of:

transmitting a series of ultrasonic waves toward the moving scatterer;

receiving a series of ultrasonic waves reflected back by the moving scatterer;

converting the reflected back series of ultrasonic waves into a corresponding series of echo signals;

identifying in a first echo signal a zero-crossover amplitude feature and a direction corresponding to such feature;

determining location of a corresponding zero-crossover amplitude feature having the same direction in successive echo signals; and deriving velocity of the scatterer from changes in the zero-crossover amplitude feature location among the successive echo signals.

2. A method of measuring the velocity of moving scatterers using ultrasound, comprising the steps of:

transmitting ultrasonic waves toward the moving scatterers;

receiving a superposition of multiple ultrasonic waves reflected back by the moving scatterers;

converting at a transducer the reflected back waves into an ensemble of echo signals having a characteristic fringe pattern of constructive and destructive interference among the multiple reflected back ultrasonic waves corresponding to the ensemble;

repeating the steps of transmitting, receiving, and converting to achieve a sequence of ensembles of echo signals;

identifying a zero-crossover and a direction of such cross-over in one ensemble of the sequence of ensembles;

tracking the location of a corresponding zero-crossover of the same direction in adjacent ensembles; and deriving velocity of the scatterers from changes in the zero-crossover location among successive ensembles.

3. The method of claim 2, further comprising the steps of storing raw data received from the transducer as said ensemble and binning sequential ensembles to arrange raw data of the ensembles so as to correlate depth with one storage dimension and direction with another storage dimension; and wherein the step of repeating further comprising repeating the steps of storing and binning.

* * * * *